(12) United States Patent
Merkel et al.

(10) Patent No.: US 9,914,680 B2
(45) Date of Patent: *Mar. 13, 2018

(54) METHOD FOR PRODUCING FLUORINATED ORGANIC COMPOUNDS

(71) Applicant: HONEYWELL INTERNATIONAL INC., Morristown, NJ (US)

(72) Inventors: Daniel C. Merkel, West Seneca, NY (US); Robert C. Johnson, Lancaster, NY (US); Hsueh Sung Tung, Getzville, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/704,491

(22) Filed: May 5, 2015

(65) Prior Publication Data

US 2015/0361014 A1    Dec. 17, 2015

Related U.S. Application Data

(63) Continuation of application No. 12/631,728, filed on Dec. 4, 2009, now Pat. No. 9,024,092, which is a continuation-in-part of application No. 11/619,592, filed on Jan. 3, 2007, now Pat. No. 8,084,653, said application No. 12/631,728 is a continuation of application No. 12/338,466, filed on Dec. 18, 2008, now abandoned.

(60) Provisional application No. 60/755,485, filed on Jan. 3, 2006, provisional application No. 61/021,121, filed on Jan. 15, 2008.

(51) Int. Cl.
*C07C 17/013* (2006.01)
*C07C 17/087* (2006.01)
*C07C 19/10* (2006.01)

(52) U.S. Cl.
CPC .......... *C07C 17/013* (2013.01); *C07C 17/087* (2013.01); *C07C 19/10* (2013.01)

(58) Field of Classification Search
None
See application file for complete search history.

(56) References Cited

U.S. PATENT DOCUMENTS

| | | | | |
|---|---|---|---|---|
| 5,902,912 A * | 5/1999 | Tung | ...................... | B01J 3/00 570/164 |
| 8,084,653 B2 * | 12/2011 | Tung | .................... | C07C 17/00 570/123 |
| 8,664,455 B2 * | 3/2014 | Merkel | ................ | C07C 17/087 570/156 |
| 8,916,733 B2 * | 12/2014 | Merkel | ................ | C07C 17/087 570/167 |

FOREIGN PATENT DOCUMENTS

WO    WO2007079431    *    7/2007

* cited by examiner

*Primary Examiner* — Clinton Brooks
(74) *Attorney, Agent, or Firm* — Bruce O. Bradford

(57) ABSTRACT

Provided is a process for making 2-chloro-1,1,1,2-tetrafluoropropane. The process has the step of hydrofluorinating 2-chloro-3,3,3-trifluoropropene in the presence of a catalyst selected from the group consisting of $SbCl_3$, $SbCl_5$, $SbF_5$, $TiCl_4$, $SnCl_4$, $Cr_2O_3$, and fluorinated $Cr_2O_3$.

14 Claims, No Drawings

METHOD FOR PRODUCING FLUORINATED ORGANIC COMPOUNDS

CROSS-REFERENCE TO RELATED APPLICATIONS

This application is a Continuation of U.S. application Ser. No. 12/631,728, filed Dec. 4, 2009, (now U.S. Pat. No. 9,024,092, issued May 5, 2015), which application is a Continuation-In-Part (CIP) of U.S. application Ser. No. 11/619,592, filed Jan. 3, 2007, (now U.S. Pat. No. 8,084,653, issued Dec. 27, 2011), which in turn, claims the priority benefit of U.S. Provisional Application No. 60/755,485, filed Jan. 3, 2006. Application Ser. No. 12/631,728 is also a continuation of U.S. application Ser. No. 12/338,466, filed Dec. 18, 2008 (abandoned), which in turn claims the priority benefit of U.S. Provisional Application No. 61/021,121, filed Jan. 15, 2008. Each of these applications is incorporated herein by reference.

BACKGROUND OF THE INVENTION

1. Field of the Invention

The present invention relates to a process for making 2-chloro-1,1,1,2-tetrafluoropropane. The present invention further relates to a process for making 2-chloro-1,1,1,2-tetrafluoropropane via hydrofluorination of 2-chloro-3,3,3-trifluoropropene with high single-pass conversion.

2. Description of the Related Art

The refrigerant and blowing agent 2,3,3,3-tetrafluoropropene (1234yf) is produced from the dehydrochlorination of 2-chloro-1,1,1,2-tetrafluoropropane (244bb). 244bb may be manufactured from 2-chloro-3,3,3-trifluoropropene (1233xf).

When conversion of 2-chloro-1,1,1,2-tetrafluoropropane from 2-chloro-3,3,3-trifluoropropene is low, 2-chloro-1,1,1,2-tetrafluoropropane and 2-chloro-3,3,3-trifluoropropene are present in admixture in product streams. 2-chloro-1,1,1,2-tetrafluoropropane and 2-chloro-3,3,3-trifluoropropene exhibit similar boiling points and azeotrope-like properties that make them difficult to separate via standard techniques such as conventional distillation.

One method of addressing the problem of low conversion is to increase recycle of product streams to the reactor so that additional conversion is obtained. The increased recycle would require process equipment to be increased in size and scale to maintain a desired level or product output, and, thus significantly increase manufacturing cost. In addition, the separation of components in the product stream is difficult.

It would be desirable to have a process for making 2-chloro-1,1,1,2-tetrafluoropropane from 2-chloro-3,3,3-trifluoropropene at higher single-pass conversion levels.

SUMMARY OF THE INVENTION

Provided is a process for making 2-chloro-1,1,1,2-tetrafluoropropane. The process has the step of hydrofluorinating 2-chloro-3,3,3-trifluoropropene in the presence of a catalyst selected from the group consisting of $SbCl_3$, $SbCl_5$, $SbF_5$, $TiCl_4$, $SnCl_4$, $Cr_2O_3$, and fluorinated $Cr_2O_3$. Preferably, the process is performed as a continuous process.

DETAILED DESCRIPTION OF THE INVENTION

In the process of the present invention, selected catalysts are employed to enhance the single-pass conversion of 2-chloro-3,3,3-trifluoropropene to 2-chloro-1,1,1,2-tetrafluoropropane via HF addition across the double bond of 2-chloro-3,3,3-trifluoropropene. The catalysts are the following: $SbCl_3$, $SbCl_5$, $SbF_5$, $TiCl_4$, $SnCl_4$, $Cr_2O_3$, and fluorinated $Cr_2O_3$.

The catalyst may be supported or in bulk form (unsupported). Useful catalyst supports include carbon, alumina, fluorinated alumina, aluminum fluoride, alkaline earth metal oxides, fluorinated alkaline earth metals, zinc oxide, zinc fluoride, tin oxide, and tin fluoride.

The catalyst optionally may be activated prior to and during use. Useful activating agents include anhydrous hydrogen fluoride and chlorine. The catalyst is kept activated by the continuous or batch addition of an oxidizing agent such as $Cl_2$.

The hydrofluorination process may be carried out in a vapor phase or a liquid phase.

In vapor-phase hydrofluorination, HF (hydrogen fluoride gas) is fed continuously through the catalyst bed. After a short time with only the HF feed stream, 2-chloro-3,3,3-trifluoropropene is fed continuously through the catalyst bed at a ratio of about 1:1 to about 1:30 and preferably from about 1:2 to about 1:15 (2-chloro-3,3,3-trifluoropropene/HF mole ratio). The reaction between HF and 2-chloro-3,3,3-trifluoropropene is carried out at a temperature from about 30° C. to about 200° C. (preferably from about 50° C. to about 120° C.) and at a pressure of about 5 psia to about 200 psia (pounds per square inch absolute) (preferably from about 30 psia to about 175 psia). The catalyst may be supported on a substrate, such as on activated carbon, or may be unsupported or free-standing. The catalyst may (or may not) have to be activated with anhydrous hydrogen fluoride HF (hydrogen fluoride gas) and/or $Cl_2$ (chlorine gas) before use depending on the state of the catalyst. If necessary, the catalyst can be kept activated by the continuous or batch addition of $Cl_2$ or a similar oxidizing agent.

In liquid phase hydrofluorination, the catalyst is charged in a liquid form to a reactor and optionally activated with HF. The activated catalyst is then heated to the desired reaction temperature of about 30° C. to about 200° C. (preferably from about 50° C. to about 120° C.) and the pressure is kept between about 15 psia to about 200 psia (preferably from about 50 psia to about 175 psia). After a short time with only HF feed, a 2-chloro-3,3,3-trifluoropropene feed stream is fed continuously through the catalyst bed at a ratio of about 1:1 to about 1:30 and preferably about 1:2 to about 1:15 (2-chloro-3,3,3-trifluoropropene/HF mole ratio). If necessary, the catalyst can be kept activated by the continuous or batch addition of $Cl_2$ or a similar oxidizing agent.

Enhanced or improved single-pass conversion of 2-chloro-3,3,3-trifluoropropene to 2-chloro-1,1,1,2-tetrafluoropropane is an important feature of the present invention. The hydrofluorination reaction is preferably carried out to attain a conversion of about 70% or more, preferably about 90% or more, and most preferably about 93% or more. Conversion is calculated by the number of moles of reactant (2-chloro-3,3,3-trifluoropropene) consumed divided by number of moles of reactant (2-chloro-3,3,3-trifluoropropene) fed to the reactor multiplied by 100. The selectivity for 2-chloro-1,1,1,2-tetrafluoropropane attained is preferably about 60% or more and most preferably about 80% or more. Selectivity is calculated by number of moles of product (2-chloro-1,1,1,2-tetrafluoropropane) formed divided by number of moles of reactant consumed.

Hydrofluorination is preferably carried out in a corrosion-resistant reaction vessel. Examples of corrosion-resistant materials are Hastelloy, Nickel, Incoloy, Inconel, Monel and fluoropolymer linings. The vessel may have a fixed or a fluidized catalyst bed. If desired, inert gases such as nitrogen or argon may be employed in the reactor during operation.

The following are examples of the present invention and are not to be construed as limiting. Unless otherwise indicated, all percentages and parts are by weight.

EXAMPLES

Example 1

The vapor phase fluorination of the 2-chloro-3,3,3-trifluoropropene (1233xf)+HF→2-chloro-1,1,1,2-tetrafluoropropane (244bb) was carried out. The fluorination catalyst for the experiment was 50 wt % $SbCl_5$ impregnated on 50 wt % Calgon PCB activated carbon.

Several kilograms of 50 weight % $SbCl_5$ on activated carbon were produced in the lab. The catalyst was first passed through a 10-mesh sieve to remove fines. A total of 2272.6 grams (or about 2800 cc) was charged to two 2-inch vapor-phase pipe reactors in series and installed in a sand bath for controlled heating.

The catalyst was activated by adding a minimum of a 5:1 mole ratio of HF to $SbCl_5$, followed by a $Cl_2$ addition of a minimum of a 3:1 mole ratio of $Cl_2$ to $SbCl_5$. Finally, a large excess of HF was passed through the catalyst bed for 2 hours.

The reaction was run using 2-chloro-3,3,3-trifluoropropene crude raw material with various compositions as organic feed to produce 2-chloro-1,1,1,2-tetrafluoropropane. The reactor effluent was collected in a distillation column before removal of excess HF. During the experiment, a 93.5% conversion of 2-chloro-3,3,3-trifluoropropene was achieved. The maximum selectivity of 2-chloro-1,1,1,2-tetrafluoropropane achieved was 98.4% on a molar basis. The reaction ran continuously for 76.5 hrs without attempting catalyst regeneration with $Cl_2$. The catalyst began showing signs of deactivation after about 65 hours on-stream time. The experimental data and reaction conditions are shown below in Tables 1A to 1D.

TABLE 1A

| On-stream time (hrs) | T (° C.) | P (Mpa) | Catalyst | 1233xf feed rate (mmole/min) | 1233xf feed rate (g/hr) | HF feed rate (mmole/min) | HF feed rate (g/hr) | mole ratio HF:1233xf | Catalyst (ml) | Contact Time (sec) |
|---|---|---|---|---|---|---|---|---|---|---|
| 1-23 | 72 | 0.33 | $SbCl_5$/C | 12.0 | 95.3 | 185.2 | 222.3 | 15.5 | 2800 | 99 |
| 23-29 | 72 | 0.33 | $SbCl_5$/C | 18.3 | 145.2 | 215.5 | 258.6 | 11.8 | 2800 | 84 |
| 29-42 | 72 | 0.33 | $SbCl_5$/C | 23.4 | 186.0 | 241.9 | 290.3 | 10.3 | 2800 | 74 |
| 42-53 | 74 | 0.33 | $SbCl_5$/C | 30.2 | 240.4 | 275.9 | 331.1 | 9.1 | 2800 | 64 |
| 53-60 | 76 | 0.33 | $SbCl_5$/C | 39.3 | 322.1 | 317.5 | 381.0 | 8.1 | 2800 | 54 |
| 60-65.5 | 77 | 0.33 | $SbCl_5$/C | 48.1 | 394.6 | 400.7 | 480.8 | 8.3 | 2800 | 43 |
| 65.5-73.5 | 80 | 0.33 | $SbCl_5$/C | 51.1 | 408.2 | 404.5 | 485.4 | 7.9 | 2800 | 42 |
| 73.5-76.5 | 79 | 0.33 | $SbCl_5$/C | 33.9 | 281.2 | 355.3 | 426.4 | 10.5 | 2800 | 49 |

TABLE 1B

| | Feed composition (GC area %) | | | | | |
|---|---|---|---|---|---|---|
| On-stream Time (hrs) | 1234yf/245cb | 244bb | 1233xf | 1232xf | 1223xd | others |
| 1-23 | 0 | 0.31 | 82.41 | 17.03 | 0 | 0.25 |
| 23-29 | 0 | 0.31 | 82.41 | 17.03 | 0 | 0.25 |
| 29-42 | 0 | 0.31 | 82.41 | 17.03 | 0 | 0.25 |
| 42-53 | 0 | 0.31 | 82.41 | 17.03 | 0 | 0.25 |
| 53-60 | trace | 31.08 | 68.92 | 0 | 0 | 0 |
| 60-65.5 | trace | 31.08 | 68.92 | 0 | 0 | 0 |
| 65.5-73.5 | 0.69 | 21.41 | 77.36 | 0 | trace | 0.54 |
| 73.5-76.5 | 0.03 | 38.86 | 61.09 | 0 | 0 | 0.02 |

TABLE 1C

| | Reactor Effluent Composition (GC area %) | | | | | |
|---|---|---|---|---|---|---|
| On-stream Time (hrs) | 1234yf/245cb | 244bb | 1233xf | 1232xf | 1223xd | others |
| 1-23 | 3.0 | 86.2 | 7.5 | 0.2 | 0.1 | 3.0 |
| 23-29 | 1.3 | 91.7 | 5.1 | 0.2 | 0.1 | 1.7 |
| 29-42 | 0.9 | 92.1 | 4.8 | 0.2 | 0.0 | 1.9 |
| 42-53 | 0.9 | 91.3 | 5.9 | 0.1 | 0.0 | 1.8 |
| 53-60 | 0.6 | 92.0 | 7.1 | 0.0 | 0.0 | 0.4 |
| 60-65.5 | 0.7 | 90.0 | 8.9 | 0.0 | 0.0 | 0.5 |
| 65.5-73.5 | 1.6 | 87.1 | 10.2 | 0.0 | trace | 1.1 |
| 73.5-76.5 | 1.4 | 86.3 | 11.6 | 0.0 | 0.0 | 0.8 |

TABLE 1D

| 1233xf Conversion | 1232xf Conversion | Selectivities (molar basis presuming GC area % = wt %) | | | | |
|---|---|---|---|---|---|---|
| | | 1234yf/245cb | 244bb | 1232xf | 1223xd | others |
| 89.9 | 99.0 | 3.9 | 92.6 | NA | 0.1 | 3.2 |
| 93.2 | 98.8 | 1.6 | 96.4 | NA | 0.0 | 1.8 |
| 93.5 | 99.0 | 1.2 | 96.6 | NA | 0.0 | 2.0 |
| 92.0 | 99.3 | 1.1 | 96.9 | NA | 0.0 | 1.9 |
| 83.8 | NA | 1.0 | 98.4 | 0.0 | 0.0 | 0.6 |
| 82.8 | NA | 1.2 | 98.1 | 0.0 | 0.0 | 0.7 |
| 81.5 | NA | 1.5 | 97.8 | 0.0 | 0.0 | 0.7 |
| 75.1 | NA | 3.1 | 95.5 | 0.1 | 0.0 | 1.6 |

Example 2

The liquid phase fluorination reaction of 2-chloro-3,3,3-trifluoropropene (1233xf)+HF→2-chloro-1,1,1,2-tetrafluoropropane (244bb) was carried out. The fluorination catalyst for the experiment was $SbCl_5$.

About 6100 grams of $SbCl_5$ were contained in a Teflon™-lined liquid phase reactor (Teflon is a trademark of E.I. duPont de Nemours & Co) equipped with a 2-inch ID (inside diameter) packed column and a condenser. The reactor was 2.75-inch ID×36-inch L (length). Initially, a greater than 5:1 mole ratio of HF was added to the reactor to fluorinate the catalyst. A greater than 3:1 mole ratio of $Cl_2$ was then added to the reactor to ensure that the catalyst was brought back to a pentavalent state. The reactor was heated to about 85° C.-87° C. HF feed was started first. When an additional 1.3 lbs of HF had been added the 2-chloro-3,3,3-trifluoropropene feed was started. The purity of the 2-chloro-3,3,3-trifluoropropene feed stock was about 98 GC area % (gas chromatograph). The experiment ran continuously for 71 hours. For this run, chlorine was fed batchwise about every 4 hours throughout the run to keep the catalyst active. The HF and 2-chloro-3,3,3-trifluoropropene feeds were varied during the run. The feeds averaged 0.495 lbs/hr HF, and 0.408 lbs/hr 2-chloro-3,3,3-trifluoropropene (chlorine was 5.4% by weight of organic) for a 7.9/1 ratio of HF/2-chloro-3,3,3-trifluoropropene, and 135 seconds residence time at the beginning of the run. In the middle of the run, the feeds averaged 0.843 lbs/hr HF (pounds/hour) and 0.66 lbs/hr 2-chloro-3,3,3-trifluoropropene (chlorine was 3.3% by weight of organic) for a 8.33/1 ratio of HF/2-chloro-3,3,3-trifluoropropene, and 80 seconds residence time. For the end of the run, the rate was increased. The feeds for this period averaged 1.42 lbs/hr HF and 1.24 lbs/hr 2-chloro-3,3,3-trifluoropropene (chlorine was 2% by weight of organic) for a 7.5/1 ratio of HF/2-chloro-3,3,3-trifluoropropene, and 47 seconds residence time. The level of unreacted 2-chloro-3,3,3-trifluoropropene appeared to increase late in the run, which could have been the result of lower $Cl_2$ level or shorter residence time.

The reactor temperature range for the experiment was 78-91° C. and the pressure range was 85 psig-115 psig (pounds per square inch gauge).

The following Table 2 contains the 2-chloro-3,3,3-trifluoropropene conversion and product selectivity data:

TABLE 2

| | | | (Conversion and Selectivity on a Molar Basis) | | | | |
|---|---|---|---|---|---|---|---|
| elapsed time (Hours) | HFC245cb Selectivity | HCFC244bb Selectivity | HCFC1233xf Conversion | HCFC235da Selectivity | HCFC1223xd Selectivity | Others Selectivity | Temp ° C. |
| 2 | 64.8 | 24.2 | 99.3 | 0.0 | 0.0 | 11.1 | 87.1 |
| 3 | 68.2 | 24.2 | 99.2 | 0.9 | 4.8 | 1.9 | 90.5 |
| 4 | 67.5 | 24.3 | 99.8 | 0.6 | 3.6 | 3.9 | 90.2 |
| 5 | 64.6 | 30.0 | 99.9 | 1.2 | 3.1 | 1.1 | 90.4 |
| 6 | 67.4 | 27.2 | 99.8 | 1.2 | 3.1 | 1.0 | 85.7 |
| 8 | 82.8 | 15.6 | 99.7 | 0.4 | 0.8 | 0.5 | 78.9 |
| 9 | 78.5 | 20.2 | 99.9 | 0.3 | 0.6 | 0.4 | 78.9 |
| 10 | 65.4 | 32.3 | 99.6 | 0.6 | 1.0 | 0.6 | 83.2 |
| 11 | 61.8 | 35.8 | 99.0 | 0.6 | 1.0 | 0.7 | 78.5 |
| 12 | 64.8 | 33.7 | 99.3 | 0.5 | 0.6 | 0.4 | 79.6 |
| 13.5 | 61.6 | 37.0 | 99.8 | 0.5 | 0.5 | 0.4 | 80.9 |
| 14 | 62.1 | 36.5 | 99.7 | 0.5 | 0.5 | 0.5 | 81.3 |
| 15 | 61.9 | 36.8 | 99.6 | 0.5 | 0.4 | 0.4 | 78.9 |
| 16 | 29.1 | 68.3 | 99.5 | 1.3 | 0.6 | 0.7 | 86.9 |
| 17 | 30.5 | 67.3 | 98.6 | 1.2 | 0.5 | 0.5 | 88.5 |
| 18 | 24.4 | 73.0 | 98.8 | 1.5 | 0.6 | 0.5 | 84.5 |
| 19 | 31.0 | 66.1 | 98.3 | 1.6 | 0.7 | 0.5 | 87.5 |
| 20 | 28.7 | 66.8 | 99.8 | 2.5 | 1.2 | 0.9 | 84.5 |
| 21 | 33.8 | 62.9 | 99.7 | 1.8 | 0.9 | 0.6 | 86.9 |
| 22 | 51.6 | 46.6 | 99.5 | 0.9 | 0.5 | 0.5 | 86.6 |
| 23 | 54.3 | 45.1 | 99.7 | 0.2 | 0.1 | 0.2 | 85.6 |
| 24 | 28.3 | 70.1 | 99.5 | 0.8 | 0.4 | 0.4 | 86.9 |
| 25 | 23.0 | 74.8 | 99.0 | 1.1 | 0.6 | 0.5 | 86.4 |
| 26 | 16.0 | 76.2 | 98.3 | 3.6 | 2.8 | 1.3 | 86.3 |
| 27 | 20.8 | 73.2 | 98.3 | 2.7 | 2.1 | 1.2 | 85.5 |
| 28 | 12.0 | 78.3 | 99.0 | 3.2 | 2.7 | 3.8 | 87 |
| 29 | 11.9 | 79.8 | 98.7 | 2.1 | 2.0 | 4.2 | 87.9 |
| 30 | 11.0 | 80.8 | 98.6 | 2.1 | 2.0 | 4.2 | 87.1 |
| 31 | 13.9 | 81.7 | 98.2 | 0.8 | 1.0 | 2.6 | 86.2 |
| 32 | 10.2 | 86.6 | 99.3 | 0.4 | 0.7 | 2.2 | 85.9 |
| 33 | 9.4 | 87.9 | 98.8 | 0.2 | 1.4 | 1.0 | 85.5 |
| 34 | 12.6 | 85.8 | 98.5 | 0.1 | 0.7 | 0.8 | 85.4 |
| 35 | 15.1 | 83.6 | 98.1 | 0.1 | 0.5 | 0.7 | 85.3 |
| 36 | 4.3 | 92.3 | 98.2 | 0.1 | 2.2 | 1.1 | 85.2 |
| 37 | 4.7 | 92.3 | 97.9 | 0.1 | 1.8 | 1.2 | 84.9 |
| 38 | 4.8 | 92.7 | 97.9 | 0.1 | 1.5 | 1.0 | 85.4 |
| 39.5 | 8.6 | 89.5 | 97.8 | 0.0 | 0.1 | 1.8 | 85.1 |
| 41.7 | 17.1 | 81.4 | 98.1 | 0.0 | 0.6 | 0.9 | 85 |
| 42.7 | 14.0 | 85.7 | 97.8 | 0.0 | 0.1 | 0.3 | 83.6 |
| 44.7 | 20.4 | 79.1 | 98.1 | 0.0 | 0.0 | 0.4 | 80.6 |
| 46 | 6.0 | 92.5 | 98.3 | 0.0 | 0.9 | 0.5 | 84.2 |
| 47.5 | 6.1 | 91.1 | 99.7 | 0.0 | 1.5 | 1.3 | 86.2 |
| 48 | 6.2 | 91.5 | 99.9 | 0.0 | 1.3 | 1.0 | 87.1 |
| 49 | 10.6 | 86.8 | 98.9 | 0.0 | 1.7 | 0.9 | 86.9 |
| 50 | 7.2 | 91.0 | 98.1 | 0.0 | 1.1 | 0.7 | 86.6 |
| 51 | 10.9 | 88.4 | 97.7 | 0.0 | 0.3 | 0.4 | 86.7 |
| 52 | 13.9 | 82.9 | 98.7 | 0.0 | 2.3 | 0.9 | 89.3 |
| 53 | 12.7 | 86.0 | 97.9 | 0.0 | 0.6 | 0.8 | 87.5 |
| 54 | 9.5 | 89.4 | 97.7 | 0.0 | 0.5 | 0.6 | 88 |
| 55 | 6.6 | 92.2 | 98.3 | 0.0 | 0.6 | 0.7 | 87.1 |
| 56 | 6.8 | 89.6 | 98.1 | 0.0 | 2.7 | 1.0 | 87.4 |
| 57 | 7.5 | 91.1 | 97.6 | 0.0 | 0.7 | 0.7 | 87.7 |

TABLE 2-continued (Conversion and Selectivity on a Molar Basis)

| elapsed time (Hours) | HFC245cb Selectivity | HCFC244bb Selectivity | HCFC1233xf Conversion | HCFC235da Selectivity | HCFC1223xd Selectivity | Others Selectivity | Temp ° C. |
|---|---|---|---|---|---|---|---|
| 58.1 | 5.4 | 91.6 | 99.8 | 0.1 | 1.4 | 1.6 | 87.6 |
| 60 | 6.2 | 92.7 | 98.8 | 0.0 | 0.2 | 0.9 | 87.8 |
| 65.3 | 0.0 | 99.4 | 96.9 | 0.0 | 0.2 | 0.3 | 88 |
| 66 | 5.2 | 91.7 | 99.7 | 0.1 | 2.0 | 1.0 | 87.2 |
| 69 | 3.3 | 96.2 | 96.1 | 0.1 | 0.2 | 0.3 | 88 |
| 70 | 3.0 | 95.1 | 95.3 | 0.1 | 1.3 | 0.5 | 87.9 |
| 71 | 2.8 | 95.4 | 96.8 | 0.0 | 0.4 | 1.4 | 88.5 |

Example 3

Example 3 used the same equipment as Example 2.

About 5615 grams of SbCl$_5$ were contained in the same reactor as that of Example 2. The reactor was heated to about 85° C.-87° C. HF feed was started first. After about 1.5 lbs of HF had been added, the 2-chloro-3,3,3-trifluoropropene feed was started. The purity of the 2-chloro-3,3,3-trifluoropropene feed stock was about 97.3 GC area %. The experiment ran continuously for 71 hours. For this run, Cl$_2$ was fed batchwise about every 4 hours throughout the run to keep the catalyst active.

The Run # for this experiment was 36b. Conversion was immediately above 98%, and remained that way throughout the rest of the run (through Friday shut-down). The catalyst charge was left hot over the weekend, and operation resumed on Monday (now called Run #37), and similar high conversion was observed throughout the week. About 123 pounds of acid-free 2-chloro-1,1,1,2-tetrafluoropropane crude was collected between runs #36b and its continuation as Run #37 the following week.

The reactor temperature range for the experiment was 78° C.-86° C. and the pressure range was 70 psig-105 psig. The organic crude material collected from the run was run on a gas chromatograph and exhibited the following GC analysis.

The following Tables 3A and 3B set forth the 2-chloro-3,3,3-trifluoropropene (1233xf) conversion and product selectivity data.

TABLE 3A (Run #36b, Conversion and Selectivity on a Molar Basis)

| Elapsed Time (Hours) | Gas Bag # | Temp (° C.) | HF/Org mole ratio | molar selectivity HFC245cb | molar selectivity HCFC244bb | molar conversion HCFC1233xf | molar selectivity HCFC235da | molar selectivity HCFC1232xf | molar selectivity HCFC1223xd |
|---|---|---|---|---|---|---|---|---|---|
| 35.3 | 1 | 84.1 | 0.64 | 0.26 | 98.69 | 0.01 | 0.02 | 0.06 | 35.3 |
| 36.3 | 2 | 85 | 0.43 | 0.54 | 98.70 | 0.01 | 0.00 | 0.01 | 36.3 |
| 37.3 | 3 | 85.2 | 0.55 | 0.41 | 98.94 | 0.01 | 0.01 | 0.02 | 37.3 |
| 38.6 | 4 | 85.6 | 0.44 | 0.51 | 98.71 | 0.01 | 0.00 | 0.02 | 38.6 |
| 39.2 | 5 | 83.6 | 0.30 | 0.63 | 97.77 | 0.01 | 0.01 | 0.03 | 39.2 |
| 39.7 | 6 | 85.5 | 0.25 | 0.70 | 97.26 | 0.01 | 0.01 | 0.02 | 39.7 |
| 40.8 | 7 | 86.9 | 0.36 | 0.59 | 98.08 | 0.01 | 0.00 | 0.03 | 40.8 |
| 41.6 | 8 | 83 | 0.55 | 0.44 | 98.94 | 0.00 | 0.00 | 0.01 | 41.6 |
| 42.4 | 9 | 85.9 | 0.40 | 0.58 | 98.40 | 0.00 | 0.00 | 0.01 | 42.4 |
| 43.4 | 10 | 85.3 | 0.37 | 0.61 | 98.42 | 0.00 | 0.00 | 0.00 | 43.4 |
| 44.75 | 11 | 83.1 | 0.29 | 0.70 | 98.37 | 0.00 | 0.01 | 0.01 | 44.75 |
| 45.5 | 12 | 80 | 0.23 | 0.76 | 98.44 | 0.00 | 0.00 | 0.00 | 45.5 |
| 46.5 | 13 | 81.7 | 0.21 | 0.76 | 98.40 | 0.00 | 0.00 | 0.01 | 46.5 |
| 47.5 | 14 | 81.3 | 0.19 | 0.79 | 98.21 | 0.00 | 0.00 | 0.01 | 47.5 |

TABLE 3B (Run #37, Conversion and Selectivity on a Molar Basis)

| Elapsed Time (Hours) | Gas Bag # | Temp (° C.) | HF/Org mole ratio | molar selectivity HFC245cb | molar selectivity HCFC244bb | molar conversion HCFC1233xf | molar selectivity HCFC235da | molar selectivity HCFC1232xf | molar selectivity HCFC1223xd |
|---|---|---|---|---|---|---|---|---|---|
| 1.3 | 1 | 87.5 | 11.84 | 0.16 | 0.82 | 98 | 0.002 | 0.002 | 0.005 |
| 2.4 | 2 | 85.2 | 6.09 | 0.10 | 0.89 | 98 | 0.002 | 0.002 | 0.005 |
| 3.25 | 3 | 86.5 | 5.49 | 0.13 | 0.84 | 98 | 0.003 | 0.002 | 0.013 |
| 4.4 | 4 | 83.2 | 7.03 | 0.10 | 0.88 | 98 | 0.003 | 0.002 | 0.017 |
| 5.4 | 5 | 83.3 | 8.80 | 0.10 | 0.88 | 98 | 0.002 | 0.001 | 0.008 |
| 6.4 | 6 | 81.5 | 8.00 | 0.08 | 0.90 | 98 | 0.002 | 0.001 | 0.004 |
| 7.4 | 7 | 79.9 | 20.74 | 0.08 | 0.90 | 98 | 0.002 | 0.001 | 0.008 |
| 8.3 | 8 | 80 | 7.54 | 0.07 | 0.92 | 98 | 0.001 | 0.001 | 0.004 |
| 9.3 | 9 | 81.3 | 4.44 | 0.09 | 0.90 | 98 | 0.001 | 0.001 | 0.003 |
| 10.3 | 10 | 85.1 | 3.57 | 0.11 | 0.88 | 98 | 0.001 | 0.001 | 0.003 |
| 11.3 | 11 | 88 | 4.64 | 0.15 | 0.83 | 98 | 0.002 | 0.002 | 0.015 |
| 12.6 | 12 | 85.5 | 5.03 | 0.14 | 0.85 | 98 | 0.001 | 0.002 | 0.004 |

TABLE 3B-continued (Run #37, Conversion and Selectivity on a Molar Basis)

| Elapsed Time (Hours) | Gas Bag # | Temp (° C.) | HF/Org mole ratio | molar selectivity HFC245cb | molar selectivity HCFC244bb | molar conversion HCFC1233xf | molar selectivity HCFC235da | molar selectivity HCFC1232xf | molar selectivity HCFC1223xd |
|---|---|---|---|---|---|---|---|---|---|
| 13.4 | 13 | 85.3 | 4.68 | 0.10 | 0.89 | 98 | 0.001 | 0.002 | 0.003 |
| 14.3 | 14 | 82.8 | 5.08 | 0.08 | 0.91 | 98 | 0.001 | 0.002 | 0.003 |
| 15.3 | 15 | 83.7 | 5.63 | 0.09 | 0.89 | 98 | 0.002 | 0.001 | 0.012 |
| 16.25 | 16 | 84.2 | 7.21 | 0.08 | 0.91 | 98 | 0.001 | 0.001 | 0.004 |
| 17.4 | 17 | 86.1 | 7.86 | 0.09 | 0.91 | 98 | 0.001 | 0.001 | 0.003 |
| 18.3 | 18 | 85.7 | 8.33 | 0.07 | 0.92 | 98 | 0.001 | 0.001 | 0.002 |
| 19.3 | 19 | 86 | 7.38 | 0.09 | 0.88 | 98 | 0.003 | 0.002 | 0.018 |
| 20.3 | 20 | 87.8 | 8.27 | 0.09 | 0.90 | 98 | 0.002 | 0.001 | 0.003 |
| 21.4 | 21 | 83.4 | 10.48 | 0.08 | 0.88 | 98 | 0.002 | 0.003 | 0.003 |
| 22.4 | 22 | 88.7 | 18.21 | 0.08 | 0.91 | 98 | 0.001 | 0.001 | 0.003 |
| 23.3 | 23 | 83 | 9.26 | 0.08 | 0.90 | 98 | 0.002 | 0.001 | 0.007 |
| 24.3 | 24 | 82.9 | 7.46 | 0.06 | 0.93 | 98 | 0.001 | 0.001 | 0.004 |
| 25.3 | 25 | 81.3 | 7.19 | 0.06 | 0.94 | 98 | 0.001 | 0.001 | 0.003 |
| 26.3 | 26 | 83.9 | 8.05 | 0.05 | 0.94 | 98 | 0.001 | 0.001 | 0.003 |
| 27.3 | 27 | 81.9 | 7.61 | 0.06 | 0.92 | 98 | 0.003 | 0.001 | 0.016 |
| 28.3 | 28 | 83.8 | 6.90 | 0.06 | 0.93 | 98 | 0.001 | 0.001 | 0.003 |
| 29.3 | 29 | 83.9 | 7.18 | 0.07 | 0.93 | 98 | 0.001 | 0.001 | 0.003 |
| 30.3 | 30 | 85 | 6.23 | 0.08 | 0.92 | 97 | 0.001 | 0.001 | 0.003 |
| 31.3 | 31 | 83.4 | 6.27 | 0.06 | 0.91 | 98 | 0.003 | 0.002 | 0.016 |
| 32.3 | 32 | 82.8 | 6.66 | 0.05 | 0.94 | 98 | 0.001 | 0.001 | 0.004 |
| 34.3 | 33 | 85.2 | 5.64 | 0.06 | 0.93 | 98 | 0.001 | 0.001 | 0.003 |
| 35.3 | 34 | 86 | 5.30 | 0.07 | 0.91 | 97 | 0.001 | 0.001 | 0.008 |
| 36.3 | 35 | 84.9 | 7.23 | 0.07 | 0.92 | 97 | 0.001 | 0.001 | 0.003 |
| 37.5 | 36 | 80.7 | 7.58 | 0.06 | 0.94 | 98 | 0.001 | 0.001 | 0.002 |
| 38.3 | 37 | 82.2 | 5.81 | 0.03 | 0.97 | 98 | 0.001 | 0.002 | 0.003 |
| 39.25 | 38 | 81.9 | 6.32 | 0.04 | 0.94 | 98 | 0.002 | 0.002 | 0.013 |
| 40.25 | 39 | 82 | 6.32 | 0.04 | 0.95 | 98 | 0.002 | 0.001 | 0.006 |
| 41.5 | 40 | 81.4 | 5.77 | 0.04 | 0.94 | 98 | 0.001 | 0.001 | 0.004 |
| 42.5 | 41 | 81 | 6.20 | 0.04 | 0.95 | 98 | 0.001 | 0.001 | 0.003 |
| 43.8 | 42 | 81.4 | 8.14 | 0.03 | 0.96 | 98 | 0.001 | 0.001 | 0.003 |
| 44.7 | 43 | 80.7 | 8.14 | 0.03 | 0.97 | 98 | 0.000 | 0.001 | 0.001 |
| 45.5 | 44 | 80.9 | 6.88 | 0.03 | 0.97 | 98 | 0.000 | 0.000 | 0.001 |
| 47 | 45 | 82.8 | 7.16 | 0.14 | 0.84 | 98 | 0.003 | 0.002 | 0.010 |
| 47.8 | 46 | 82.3 | 7.70 | 0.03 | 0.96 | 98 | 0.001 | 0.000 | 0.002 |
| 48.8 | 47 | 82.3 | 7.18 | 0.03 | 0.97 | 98 | 0.000 | 0.000 | 0.001 |
| 49.8 | 48 | 82.5 | 6.67 | 0.03 | 0.97 | 98 | 0.000 | 0.000 | 0.001 |
| 50.8 | 49 | 82.8 | 6.68 | 0.03 | 0.95 | 98 | 0.002 | 0.001 | 0.013 |
| 51.8 | 50 | 82.7 | 6.84 | 0.03 | 0.97 | 98 | 0.001 | 0.000 | 0.002 |
| 53 | 51 | 81.3 | 8.09 | 0.03 | 0.97 | 98 | 0.000 | 0.000 | 0.001 |
| 54.3 | 52 | 79.8 | 8.60 | 0.03 | 0.97 | 98 | 0.000 | 0.000 | 0.001 |
| 54.8 | 53 | 81.2 | 4.22 | 0.03 | 0.95 | 98 | 0.002 | 0.001 | 0.015 |
| 56 | 54 | 81.6 | 6.75 | 0.03 | 0.97 | 98 | 0.000 | 0.000 | 0.002 |
| 56.8 | 55 | 83.6 | 6.45 | 0.03 | 0.97 | 97 | 0.000 | 0.000 | 0.001 |
| 57.8 | 56 | 84.9 | 7.03 | 0.03 | 0.97 | 97 | 0.000 | 0.000 | 0.001 |
| 58.8 | 57 | 81.5 | 7.11 | 0.04 | 0.95 | 98 | 0.001 | 0.001 | 0.009 |
| 59.8 | 58 | 82.8 | 7.11 | 0.03 | 0.97 | 98 | 0.000 | 0.000 | 0.002 |
| 60.8 | 59 | 81.1 | 6.99 | 0.02 | 0.98 | 98 | 0.000 | 0.000 | 0.001 |
| 63 | 60 | 84.2 | 7.51 | 0.02 | 0.96 | 98 | 0.001 | 0.001 | 0.010 |
| 64 | 61 | 84 | 8.79 | 0.02 | 0.97 | 98 | 0.001 | 0.000 | 0.004 |
| 65 | 62 | 82.9 | 8.79 | 0.02 | 0.97 | 98 | 0.000 | 0.000 | 0.001 |
| 66 | 63 | 82.6 | 6.44 | 0.02 | 0.98 | 98 | 0.000 | 0.000 | 0.001 |
| 67 | 64 | 83.2 | 7.33 | 0.03 | 0.94 | 98 | 0.005 | 0.001 | 0.015 |
| 68.25 | 65 | 82.1 | 5.28 | 0.04 | 0.95 | 98 | 0.002 | 0.001 | 0.004 |
| 69 | 66 | 83 | 7.22 | 0.03 | 0.96 | 98 | 0.001 | 0.000 | 0.002 |
| 70 | 67 | 82.6 | 6.63 | 0.03 | 0.97 | 98 | 0.000 | 0.000 | 0.001 |
| 71 | 68 | 82.5 | 4.98 | 0.03 | 0.96 | 98 | 0.001 | 0.000 | 0.001 |
| 72 | 69 | 82.1 | 5.28 | 0.03 | 0.95 | 98 | 0.002 | 0.001 | 0.020 |
| 73 | 70 | 81.1 | 4.75 | 0.02 | 0.97 | 98 | 0.000 | 0.001 | 0.002 |
| 74.25 | 71 | 82.2 | 4.77 | 0.03 | 0.97 | 98 | 0.000 | 0.000 | 0.001 |
| 75.1 | 72 | 87.1 | 5.20 | 0.03 | 0.97 | 98 | 0.000 | 0.000 | 0.001 |
| 75.8 | 73 | 81.3 | 4.09 | 0.03 | 0.95 | 98 | 0.001 | 0.001 | 0.016 |
| 78 | 74 | 81.4 | 8.64 | 0.02 | 0.97 | 98 | 0.000 | 0.000 | 0.002 |
| 79.1 | 75 | 80.4 | 7.16 | 0.02 | 0.98 | 98 | 0.000 | 0.000 | 0.001 |
| 80 | 76 | 83.2 | 6.11 | 0.03 | 0.96 | 98 | 0.002 | 0.000 | 0.008 |
| 81.1 | 77 | 83.4 | 6.21 | 0.02 | 0.97 | 98 | 0.000 | 0.000 | 0.002 |
| 83.25 | 78 | 84 | 7.41 | 0.02 | 0.97 | 97 | 0.000 | 0.000 | 0.001 |
| 84.3 | 79 | 85.5 | 7.17 | 0.02 | 0.96 | 98 | 0.002 | 0.000 | 0.018 |
| 85 | 80 | 84.4 | 12.16 | 0.02 | 0.98 | 98 | 0.001 | 0.000 | 0.003 |
| 86 | 81 | 82.1 | 9.15 | 0.02 | 0.98 | 98 | 0.000 | 0.000 | 0.001 |
| 87 | 82 | 81.9 | 7.69 | 0.02 | 0.98 | 98 | 0.001 | 0.000 | 0.001 |
| 88.4 | 83 | 82.4 | 4.58 | 0.02 | 0.94 | 98 | 0.007 | 0.001 | 0.031 |
| 89 | 84 | 83.4 | 9.46 | 0.02 | 0.97 | 98 | 0.001 | 0.000 | 0.004 |
| 90 | 85 | 81.5 | 7.22 | 0.02 | 0.98 | 98 | 0.001 | 0.000 | 0.001 |
| 91.2 | 86 | 82.5 | 7.09 | 0.02 | 0.98 | 98 | 0.000 | 0.000 | 0.001 |

TABLE 3B-continued (Run #37, Conversion and Selectivity on a Molar Basis)

| Elapsed Time (Hours) | Gas Bag # | Temp (° C.) | HF/Org mole ratio | molar selectivity HFC245cb | molar selectivity HCFC244bb | molar conversion HCFC1233xf | molar selectivity HCFC235da | molar selectivity HCFC1232xf | molar selectivity HCFC1223xd |
|---|---|---|---|---|---|---|---|---|---|
| 92 | 87 | 83.4 | 7.49 | 0.01 | 0.97 | 98 | 0.001 | 0.001 | 0.015 |
| 93 | 88 | 82.4 | 6.60 | 0.02 | 0.98 | 98 | 0.001 | 0.000 | 0.002 |
| 94 | 89 | 82.3 | 6.25 | 0.01 | 0.97 | 98 | 0.002 | 0.000 | 0.004 |
| 95 | 89.5 | 82.4 | 6.53 | 0.02 | 98 | 0.98 | 0.000 | 0.000 | 0.001 |
| 96.5 | 90 | 83.1 | 4.76 | 0.02 | 96 | 0.97 | 0.002 | 0.001 | 0.016 |
| 97 | 91 | 82.6 | 5.01 | 0.01 | 95 | 0.97 | 0.003 | 0.001 | 0.021 |
| 97.75 | 92 | 81 | 7.29 | 0.01 | 97 | 0.98 | 0.001 | 0.001 | 0.015 |
| 98.8 | 93 | 83.1 | 6.74 | 0.02 | 98 | 0.98 | 0.000 | 0.001 | 0.012 |
| 100.2 | 94 | 82.6 | 9.05 | 0.01 | 98 | 0.98 | 0.002 | 0.000 | 0.004 |
| 101.1 | 95 | 83.3 | 5.98 | 0.02 | 98 | 0.97 | 0.000 | 0.000 | 0.003 |
| 102.3 | 96 | 85.5 | 5.11 | 0.02 | 97 | 0.97 | 0.000 | 0.000 | 0.001 |
| 103.1 | 97 | 82.7 | 5.22 | 0.02 | 97 | 0.97 | 0.001 | 0.001 | 0.007 |
| 104 | 98 | 82.4 | 5.11 | 0.02 | 97 | 0.98 | 0.000 | 0.000 | 0.001 |
| 107 | 99 | 80.4 | 5.87 | 0.02 | 98 | 0.98 | 0.000 | 0.000 | 0.001 |
| 109 | 100 | 82.6 | 7.98 | 0.02 | 98 | 0.97 | 0.000 | 0.000 | 0.001 |
| 110 | 101 | 93.3 | 5.30 | 0.03 | 97 | 0.85 | 0.000 | 0.001 | 0.001 |
| 111 | 102 | 88.8 | 4.86 | 0.03 | 85 | 0.82 | 0.000 | 0.001 | 0.001 |
| 112 | 103 | 89.4 | 5.74 | 0.03 | 82 | 0.96 | 0.000 | 0.000 | 0.000 |
| 113 | 104 | 82.8 | 10.71 | 0.02 | 96 | 0.97 | 0.000 | 0.000 | 0.000 |
| 114 | 105 | 82.1 | 9.83 | 0.01 | 97 | 0.97 | 0.000 | 0.001 | 0.001 |

Example 4: Liquid-Phase Catalytic Fluorination of $CF_3CCl\!=\!CH_2$ (1233xf) with HF to $CF_3CFClCH_3$ (244bb)

About 327 grams of HF, about 50 grams 1233xf, and about 75 grams $SbCl_5$ were charged into a 1-L autoclave. The reaction mixture was stirred at a temperature of about 80° C. for about 3 hours under about 620 psig of pressure. After the reaction, the reactor was cooled to about 0° C. and about 300 ml water was then added slowly into the autoclave over a period of about 45 min. After complete addition of water under stirring, the reactor was cooled to room temperature and then the overhead gases were transferred to another collecting cylinder. The yield of $CF_3CFClCH_3$ was about 90% at a 1233xf conversion level of about 98%. The other major by-products were $CF_3CF_2CH_3$ (2%), and an unidentified isomer of a C4 compound of the general formula, $C_4H_3Cl_3F_4$ (8%).

Example 5: Liquid-Phase Catalytic Fluorination of $CF_3CCl\!=\!CH_2$ (1233xf) with HF to $CF_3CFClCH_3$ (244bb)

About 327 grams HF, about 50 grams 1233xf, and about 75 grams $SbCl_5$ were charged into a 1-L autoclave. The reaction mixture was stirred at 80° C. for about 3 hours under about 625 psig of pressure. After the reaction, the reactor was cooled to about 45° C. and then the overhead gas mixture was passed through a well dried KF, NaF, or $Al_2O_3$ (350 g) packed column kept at about 80° C. to strip off HF from the gas stream. The gases coming out of the column are collected in a cylinder kept in dry ice (−70° C.) bath. The yield of $CF_3CFClCH_3$ was 87% at a 1233xf conversion level of 93%. The other major by-products were $CF_3CF_2CH_3$ (1%), and an unidentified isomer of a C4 compound of the general formula, $C_4H_3Cl_3F_4$ (7%). The product, $CF_3CFClCH_3$ was isolated by distillation with 98% purity.

Example 6: Gas-Phase Catalytic Fluorination of $CF_3CCl\!=\!CH_2$ (1233xf) with HF to $CF_3CFClCH_3$ (244bb)

A 22-inch (½-inch diameter) Monel tube gas phase reactor was charged with about 120 cc of a catalyst. The reactor was mounted inside a heater with three zones (top, middle and bottom). The reactor temperature was read by a custom made 5-point thermocouple kept at the middle inside of the reactor. The inlet of the reactor was connected to a pre-heater, which was kept at about 300° C. by electrical heating. Organic (1233xf) was fed from a cylinder kept at 70° C. through a regulator, needle valve, and a gas mass-flow-meter. The organic line to the pre-heater was heat traced and kept at a constant temperature of about 73° C. by electrical heating to avoid condensation. $N_2$ was used as a diluent in some cases and fed from a cylinder through a regulator and a mass flow controller into the pre-heater. All feed cylinders were mounted on scales to monitor their weight by difference. The reactions were run at a constant reactor pressure of from about 0 to about 100 psig by controlling the flow of reactor exit gases by another research control valve. The gas mixtures exiting reactor was analyzed by on-line GC and GC/MS connected through a hotbox valve arrangements to prevent condensation. The conversion of 1233xf was from about 50% to about 65% and the selectivity to 244 isomer ($CF_3CFClCH_3$) was from about 90% to about 93% depending on the reaction conditions using 120 cc of 50 wt % $SbCl_5/C$ as the catalyst at about 65° C. to about −85° C. with a HF flow of about 50 g/h and organic flow of about 15 g/h. No $CF_3CF_2CH_3$ was observed under the reaction conditions. The catalyst is pretreated at first with 50 g/h HF at about 65° C. for about 2 hours and then with about 50 g/h HF and about 200 sccm of $Cl_2$ at about 65° C. for about 4 hours. After pre-treatment, about 50 sccm of $N_2$ is flows over a period of about 40 minutes through the catalyst bed to sweep free chlorine from the catalyst surface prior to interacting with the organic feed (1233xf). Pretreatment is considered important to many embodiments of the invention. The products were collected by flowing the reactor exit gases through a 20-60 wt % aqueous KOH scrubber solution and then trapping the exit gases from the scrubber into a cylinder kept in dry ice or liquid $N_2$. The products were then isolated by distillation. About 50 wt % $SbCl_5/C$, about 3 to about 6 wt % $FeCl_3/C$, 20 wt % $SnCl_4/C$, and about 23 wt % $TiCl_4/C$, using 4 different kind of activated carbon such as Shiro saga, Calgon, Norit, and Aldrich were used as the catalyst at from about 60 to about 150° C. Among all the catalysts used for this reaction, $Cl_2$ and HF pre-treated $SbCl_5$/C was found to be generally preferred in terms of activity. The results using $SbCl_5$ as the catalyst are shown in Table 2.

TABLE 2

Catalyzed-gas-phase transformation of $CF_3CCl=CH_2$ to $CF_3CFClCH_3$

| # | Catalyst | T (° C.) | Conv. of $CF_3CCl=CH_2$ (1233xf) | Selectivity for $CF_3CFClCH_3$ |
|---|---|---|---|---|
| 1 | 10 wt % $SbCl_5$/C | 60 | 15 | 100 |
| 2 | 20 wt % $SbCl_5$/C | 60 | 21 | 98 |
| 3 | 30 wt % $SbCl_5$/C | 60 | 32 | 98 |
| 4 | 50 wt % $SbCl_5$/C | 60 | 55 | 97 |
| 5 | 50 wt % $SbCl_5$/C | 80 | 62 | 93 |
| 6 | 50 wt % $SbCl_5$/C | 100 | 56 | 87 |
| 7 | 60 wt % $SbCl_5$/C | 60 | 59 | 91 |
| 8 | 50 wt % $SbCl_5$/NORIT RFC3 Activated Carbon | 60 | 34 | 92 |
| 9 | 50 wt % $SbCl_5$/Shiro Saga Activated Carbon | 60 | 56 | 96 |
| 10 | 50 wt % $SbCl_5$/Aldrich Activated Carbon | 60 | 57 | 94 |

Reaction conditions: 1233xf flow, 150 sccm; HF flow 50 g/h; pressure, 2.5-5.3 psig; in 1-5 reactions Calgon activated carbon is used as the catalyst support; catalyst, 120 cc. All catalysts are pre-treated with $Cl_2$ and HF prior to contacting with 1233xf.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making 2-chloro-1,1,1,2-tetrafluoropropane, comprising hydrofluorinating 2-chloro-3,3,3-trifluoropropene in the presence of a catalyst selected from the group consisting of $SbCl_3$, $SbCl_5$, $SbF_5$, $TiCl_4$, and $SnCl_4$, wherein the catalyst is activated by the addition of hydrogen fluoride and/or chlorine.

2. The process of claim 1, wherein the catalyst is in bulk form.

3. The process of claim 1, wherein the catalyst is supported.

4. The process of claim 3, wherein the support is selected from the group consisting of carbon, alumina, fluorinated alumina, or aluminum fluoride.

5. The process of claim 1 where the catalyst is activated using anhydrous hydrogen fluoride.

6. The process of claim 1 where the catalyst is activated using anhydrous chlorine.

7. The process of claim 1, wherein the hydrofluorination is vapor-phase fluorination.

8. The process of claim 7, wherein the catalyst for vapor-phase fluorination reaction is $SbCl_5$ supported on activated carbon.

9. The process of claim 7, wherein the vapor-phase fluorination reaction is carried out at a temperature of about 50° C. to about 120° C. and at a pressure of about 30 psia to about 175 psia.

10. The process of claim 7, wherein the mole ratio of hydrogen fluoride to 2-chloro-3,3,3-trifluoropropene is from about 2:1 to about 15:1.

11. The process of claim 1, wherein the hydrofluorination is liquid-phase fluorination.

12. The process of claim 11, wherein the catalyst for liquid-phase fluorination reaction is $SbCl_5$.

13. The process of claim 11, wherein the liquid-phase fluorination reaction is carried out at a temperature of about 50° C. to about 120° C. and at a pressure of about 50 psia to about 175 psia.

14. The process of claim 11, wherein the mole ratio of hydrogen fluoride to 2-chloro-3,3,3-trifluoropropene is from about 2:1 to about 15:1.

* * * * *